United States Patent [19]
Shah

[11] Patent Number: 5,800,443
[45] Date of Patent: Sep. 1, 1998

[54] APPARATUS AND METHOD FOR LOCALIZING PROSTHESES DEPLOYED IN A BODY LUMEN

[76] Inventor: Ajit Shah, 112 Crescent Ave., Portola Valley, Calif. 94028

[21] Appl. No.: 826,035

[22] Filed: Mar. 28, 1997

[51] Int. Cl.$^6$ .............................. A61F 11/00; A61M 29/00
[52] U.S. Cl. .............................. 606/108; 606/198
[58] Field of Search .................. 606/1, 108, 127, 606/106, 159, 190–200; 623/1, 11, 12

[56] References Cited

U.S. PATENT DOCUMENTS

| | | | |
|---|---|---|---|
| 4,733,665 | 3/1988 | Palmaz . | |
| 4,813,930 | 3/1989 | Elliott | 604/53 |
| 5,122,136 | 6/1992 | Guglielmi et al. | 606/32 |
| 5,176,692 | 1/1993 | Wilk et al. | 606/195 |
| 5,314,444 | 5/1994 | Gianturco | 606/195 |
| 5,415,166 | 5/1995 | Imran . | |
| 5,464,408 | 11/1995 | Duc | 606/108 |
| 5,690,643 | 11/1997 | Wijay | 606/108 |

*Primary Examiner*—Glenn K. Dawson
*Attorney, Agent, or Firm*—Fish & Neave; Nicola A. Pisano

[57] ABSTRACT

Apparatus and methods are provided for determining the location of a prosthesis previously deployed in a body lumen, and for effecting treatment associated with the prosthesis. The apparatus includes a catheter having a distal end region and at least one prosthesis locator sensor disposed on the distal end region. A therapeutic device may be provided either on the distal end region of the catheter or on a separate catheter which may be positioned over the distal end region. In one embodiment the therapeutic device is a balloon catheter, while the prosthesis locator sensor is a plurality of compliant and resilient fingers projecting perpendicularly from the circumference of the catheter. The plurality of fingers detect the presence of an edge of a prosthesis by direct electrical connection, or inductance or capacitance changes. Methods of localizing prostheses with the apparatus are also provided.

21 Claims, 3 Drawing Sheets

APPARATUS AND METHOD FOR LOCALIZING PROSTHESES DEPLOYED IN A BODY LUMEN

FIELD OF THE INVENTION

The present invention relates to methods and apparatus for determining the location within a body lumen of a previously deployed prosthesis, and more particularly, for determining the location of the prosthesis to enable positioning a dilatation or therapeutic device with respect to the previously deployed prosthesis.

BACKGROUND OF THE INVENTION

In recent years a number of vascular prostheses have been developed that may be deployed in a patients' vessel or organ following a mechanical dilatation procedure.

For example, percutaneous transluminal angioplasty (PTA) is commonly used today as an alternative treatment to traditional coronary artery bypass grafting. Typically, such procedures involve the insertion of a balloon catheter within a constricted vessel, such as a coronary artery, and dilation of the balloon to disrupt plaque lining the vessel, thereby increasing the diameter of the vessel and restoring flow therethrough. It is common practice to then deploy a vascular prosthesis, such as the Palmaz-Schatz Stent® sold by Johnson & Johnson Interventional Systems, Inc., to maintain the expanded diameter of the vessel. That stent comprises a slotted metallic tubular member that is plastically deformed using a balloon catheter to maintain the patency of the vessel.

Circumstances frequently arise, when using the above prosthesis, in which the prosthesis is not completely expanded within the vessel prior to withdrawal of the delivery catheter. It also frequently occurs that a prosthesis, once implanted within a body lumen, experiences some constriction. In these instances, it is frequently desirable to re-expand the prosthesis using a subsequently inserted balloon catheter or other means for expanding the prosthesis.

Difficulties arise, however, when trying to position a dilatation device (i.e., balloon catheter) within a previously deployed prosthesis to fully expand or re-expand the prosthesis. In particular, if the dilatation device is not properly centered within the prosthesis, the prosthesis may not be evenly expanded, thus causing the prosthesis to assume the form of a frustrum of a cone, rather than a cylinder. In extreme situations, the narrower end of this frustrum may even become tilted away from the wall of the body lumen, creating sites for enhanced thrombolytic action.

A further difficulty arises when the prosthesis was previously deployed in a tortuous vessel, since it may be difficult to determine when the dilatation device is properly centered in the prosthesis using only the two-dimensional view provided by conventional fluoroscopy and dye techniques.

In addition, it would be desirable to provide apparatus and methods for determining the location of a previously deployed prosthesis to effect further treatment. For example, U.S. Pat. No. 5,122,136 to Guglielmi et al., incorporated herein by reference, describes detachable coils for use in treating aneurysms (hereinafter "GDC aneurysm coil"). It would be desirable to provide apparatus for determining the location of a previously deployed GDC aneurysm coil, for example, to add further material within the aneurysm.

It would also be desirable to determine the location of a previously deployed prosthesis to enable repositioning of a therapeutic device. For example, it has been suggested to provide localized radiation treatment using radioactive stents. It accordingly may be advantageous to locate such stents that have been previously deployed, for example, to retrieve the stent at the end of a desired period of exposure.

In view of the foregoing, it would be desirable to provide methods and apparatus for positioning a therapeutic device within a body lumen to enable a clinician to accurately determine when the therapeutic device is properly aligned with a previously deployed prosthesis.

It further would be desirable to provide methods and apparatus for enabling a clinician to accurately deploy a dilatation device within a previously deployed prosthesis to enable uniform re-expansion of the prosthesis along its length.

In addition, it would be desirable to provide methods and apparatus for accurately determining placement of a therapeutic device within a previously deployed prosthesis, such apparatus constituting an inexpensive modification of previously known catheter systems.

SUMMARY OF THE INVENTION

In view of the foregoing, it is an object of this invention to provide apparatus and methods for positioning a therapeutic device within a body lumen to enable a clinician to accurately determine when the therapeutic device is properly aligned with a previously deployed prosthesis.

It is another object of this invention to provide methods and apparatus for enabling a clinician to accurately deploy a dilatation device within a previously deployed prosthesis to enable uniform re-expansion of the prosthesis along its length.

It is a further object of the present invention to determine the location of a previously deployed prosthesis, such as an aneurysm treatment coil or a radioactive prosthesis, to enable further treatment, such as by adding further coil material or to reposition or retrieve an isotope source.

It is a further object of the present invention to provide methods and apparatus for accurately determining placement of a therapeutic device within a previously deployed prosthesis, such apparatus constituting an inexpensive modification of previously known catheter systems.

These and other objects are accomplished by providing a catheter including elements for detecting the presence of a previously deployed prosthesis, alone or in combination with a therapeutic device. In accordance with principles of the present invention, the catheter includes a therapeutic device, e.g., a dilatation device, disposed near its distal end and at least one prosthesis locator sensor disposed adjacent to the therapeutic device.

In a first illustrative embodiment of the apparatus of the present invention, the catheter comprises a balloon catheter constructed in accordance with previously known techniques and having a prosthesis locator sensor disposed proximally of the balloon to detect the proximal edge of the prosthesis. In one embodiment, the prosthesis locator sensor comprises a plurality of compliant and resilient bristles or fingers projecting perpendicularly from the circumference of the catheter. Individual ones of the plurality of fingers are coupled to a current source that provides a low-voltage, high frequency, low amperage current. Accordingly, when two fingers having conductive elements of opposite polarity contact a metallic prosthesis, a signal is generated that alerts the clinician that the catheter has identified an edge of the prosthesis. Alternatively, the fingers and sensing system may be constructed to sense some other parameter, e.g., magnetic field, inductance, capacitance, etc., corresponding to a physical property of the prosthesis.

In accordance with the methods of the present invention, the prosthesis locator sensor may be disposed adjacent to either the distal end of the therapeutic device or proximally of the device, while the therapeutic device may comprise any suitable means (e.g., dilatation device, prosthesis retractor, detachable aneurysm coil, etc.) required to effectuate the desired treatment. If the prosthesis is located proximally of the therapeutic device, the catheter constructed in accordance with the present invention is inserted until the therapeutic device extends through the previously deployed prosthesis and the prosthesis locator sensor detects a proximal edge of the prosthesis. The catheter is then withdrawn a predetermined distance corresponding to the offset between the prosthesis locator sensor and the proximal edge of the therapeutic device.

If the sensor is located distally of the therapeutic device, the catheter is inserted through the prosthesis until the sensor detects the distal edge of the prosthesis. The catheter is then inserted further until the sensor no longer senses the prosthesis, corresponding to detection of the distal end of the prosthesis. At the point at which the sensor loses contact with the distal end of the prosthesis, the catheter is advanced distally a predetermined distance corresponding to the offset between the prosthesis locator sensor and the distal edge of the therapeutic device.

Alternative embodiments of the present invention may further include prosthesis locator sensors disposed both distally and proximally of the therapeutic device. In this embodiment, the method of use may comprise reciprocating the catheter slightly in the proximal and distal directions until the distal prosthesis locator sensor detects the distal edge during slight proximal movement of the catheter and the proximal prosthesis locator sensor detects the proximal edge of the prosthesis during slight distal movement of the catheter.

A yet further alternative embodiment includes a first catheter carrying prosthesis locator sensors near its distal end and a second catheter including a therapeutic device adapted to slide over the first catheter. Using this embodiment, the prosthesis location is determined using the first catheter which is then kept in position to serve as a guidewire for the therapeutic device. A second catheter carrying the therapeutic device is then advanced a predetermined distance relative to the first catheter to achieve a desired relation between the therapeutic device and the prosthesis.

BRIEF DESCRIPTION OF THE DRAWINGS

Further features of the invention, its nature and various advantages will be more apparent from the accompanying drawings and the following detailed description of the preferred embodiments.

DETAILED DESCRIPTION OF THE INVENTION

The present invention relates generally to methods and apparatus for localizing prostheses (e.g., stents, GDC aneurysm coils, or radioactive stents) previously deployed in a body lumen, such as a coronary artery, iliac artery, or passage of the urinary tract, for the purpose of enabling further treatment. For example, in the case of underexpanded prostheses, the apparatus of the present invention permits such prostheses to be safely and fully expanded or re-expanded.

Figure 1:
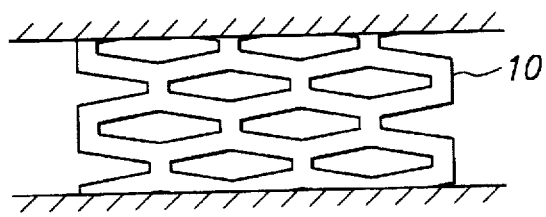
FIG. 1 depicts an illustrative previously known prosthesis suitable for re-expansion using the apparatus and methods of the present invention.

Referring to FIG. 1, a previously known balloon expandable prosthesis 10, commonly referred to as a "stent" is shown deployed in a body lumen. For purposes of illustration, prosthesis 10 may be a Palmaz-Schatz Stent® sold by Johnson & Johnson Interventional Systems, Inc., New Brunswick, N.J., or the Gianturco-Rubin Stent® sold by Cook Cardiology, Inc., Indianapolis, Ind., and generally comprises a slotted tubular member formed of stainless steel. Prosthesis 10 may alternatively be any of a number of balloon deployable prostheses described in the art.

The foregoing prostheses are deployed in a desired body lumen after angioplasty by inserting the prosthesis transluminally to the site of the blockage. First, the prosthesis is generally crimped onto the mid-section of the balloon of a balloon catheter by the clinician (or may be prepackaged crimped in such a manner). The prosthesis is then inserted transluminally to the site of the angioplasty and the balloon of the catheter on which the prosthesis is disposed is then inflated to expand the prosthesis into contact with the intima of the body lumen, thereby maintaining the lumen patent.

Two situations frequently arise with respect to such prostheses. In a first scenario, the prosthesis is underexpanded when the delivery system is withdrawn from the deployment site. This may become apparent to the clinician by observation of the expanded diameter of the prosthesis under fluoroscopy once the delivery system is removed, or may be evidenced by migration of the prosthesis within the body lumen. In such situations, the clinician may desire to re-insert the delivery system (or another mechanical dilatation device) to complete expansion of the prosthesis.

In a second scenario, the prosthesis initially is implanted at a desired diameter, but after a period of time may be observed to experience either some narrowing or migration. In these situations, the clinician may desire to re-expand the prosthesis to its initially deployed diameter, or even to further expand the prosthesis.

A drawback associated with previously known methods and apparatus for re-inserting a dilatation device within a previously deployed prosthesis relates to the inability of the clinician to accurately determine the location of the prosthesis and position the dilatation device therein. Unlike the delivery system with which the prosthesis is deployed, wherein the prosthesis may be originally centered on the dilatation device, the clinician must rely on fluoroscopy and dye methods to re-insert the dilatation device within a previously deployed prosthesis. For a number of reasons relating to the two-dimensional nature of these imaging techniques and the tortuosity of the anatomy, these methods of localizing the prosthesis may be imprecise.

Figure 2:
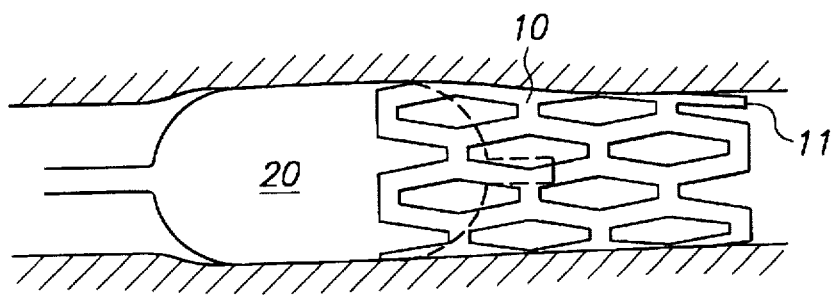
FIG. 2 is an illustrative view of an improperly positioned dilatation device unevenly re-expanding the prosthesis of FIG. 1 as may occur using previously known apparatus and methods.

As shown in FIG. 2, if dilatation device 20 is not centered within prosthesis 10 when it is expanded, the prosthesis may not be uniformly expanded along its length. In certain cases, as depicted in FIG. 2, under-expanded end 11 of prosthesis 10 may even become tilted inward towards the interior of the body lumen. If, for example, prosthesis 10 were disposed in a blood vessel, under-expanded end 11 may create turbulent flow within the vessel, thus engendering a thrombolytic reaction. It is therefore seen that while it is important to accurately position the dilatation device within a previously deployed prosthesis to re-expand the prosthesis, previously known methods provide no capability for accurately and reliably doing so.

Figure 3:
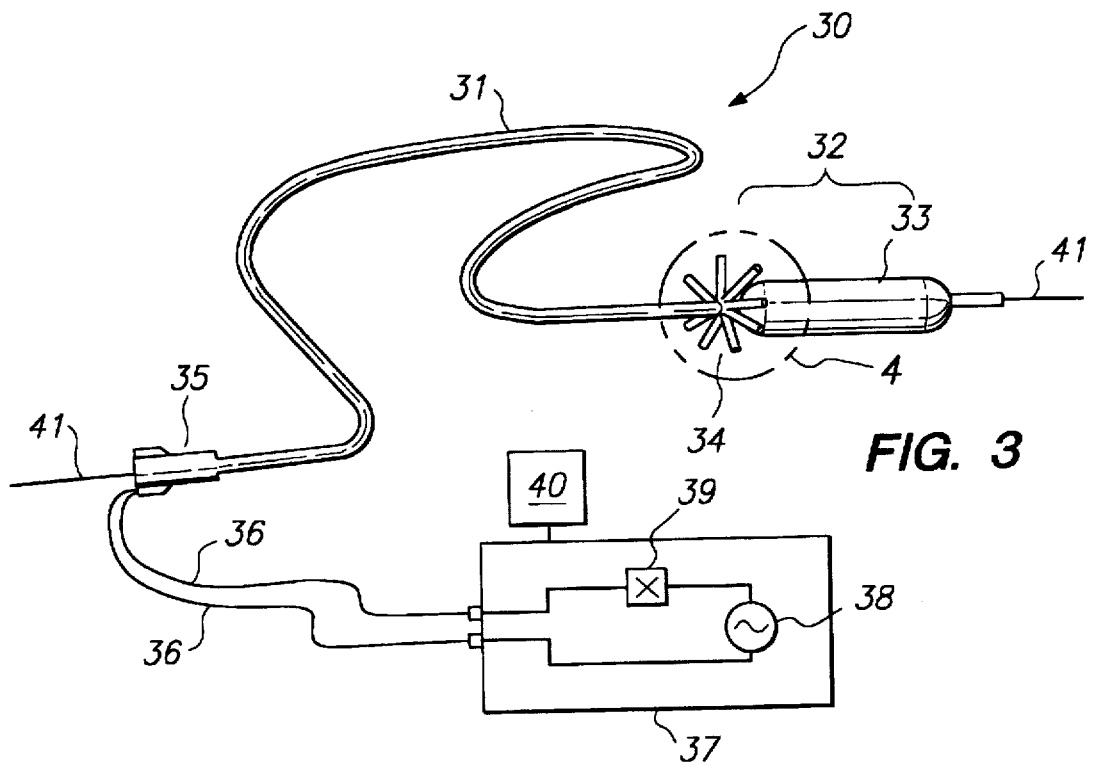
FIG. 3 is an illustrative embodiment of apparatus constructed in accordance with the principles of the present invention.

Referring now to FIG. 3, a first illustrative embodiment of apparatus 30 constructed in accordance with the present invention is described. Apparatus 30 comprises catheter 31 having distal end region 32 including a therapeutic device, i.e., balloon dilatation member 33, and prosthesis locator sensor 34. Proximal end 35 of catheter 31 has leads 36 that couple prosthesis locator sensor 34 to apparatus 37.

Apparatus 37 may contain any suitable means for providing detection of a change in a the status of the prosthesis locator sensor, including resistance, capacitance, inductance, optical or chemical, when the prosthesis locator sensor is located in the proximity of the previously deployed prosthesis. In the illustrative embodiment of FIG. 3, apparatus 37 contains a low-voltage, low current alternating current power supply 38 and current sensing circuitry 39 for detecting the presence of a current flowing across leads 36 (e.g., an ammeter). Apparatus 37 is connected to display device 40, which provides a sensory indication (e.g., visual, audible or vibratory) corresponding to the current measured flowing along leads 36, as described hereinbelow.

Catheter 31 may be a conventional balloon catheter design, which is per se known, and may include a high pressure substantially non-compliant balloon made of polyethylene terephthalate (PET) or nylon. Catheter 31 includes a connector at proximal end 37 for coupling catheter 31 to an inflation source, and a lumen for guide wire 41, as is typical for such catheters. Alternatively, balloon 33 may be replaced by another suitable dilatation device, for example, an expanding mandrel arrangement.

Figure 4:
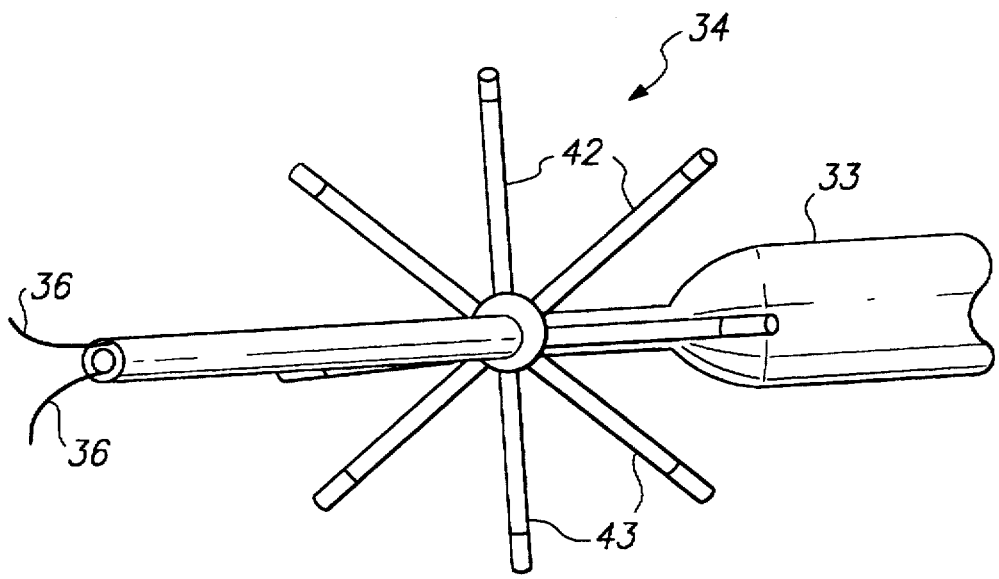
FIG. 4 is an enlarged perspective view of an illustrative prosthesis locator sensor constructed in accordance with the present invention.

In accordance with the present invention, catheter 31 includes prosthesis locator sensor 34 comprising plurality of compliant fingers or bristles 42 (shown in greater detail in FIG. 4) disposed proximally of dilatation device 33. As shown in FIG. 4, fingers 42 project perpendicularly away from catheter 32 and have a length slightly larger than the maximum prosthesis diameter or lumen diameter. Fingers 42 preferably comprise a soft, resilient material, such as silicone, so that they can bend to accommodate the diameter of the body lumen.

Each of fingers 42 includes electrically conductive element 43 disposed on its distal end that is electrically coupled via thin wires to one or the other of leads 36. The thin wires, preferably of a soft metal or alloy, are embedded in the material forming fingers 42, and are connected via one or the other of leads 36. Fingers 42 may be arranged so that alternating ones of the fingers are electrically coupled to leads 36 of opposite polarity. Alternatively, fingers 42 may be arranged so that several fingers of like polarity are grouped together around the circumference, with non-conducting fingers arranged between the groups of like polarity. Other arrangements will be apparent to one of skill in the art of electromechanical instrument design, so long as direct contact between fingers of opposite polarity is avoided.

Accordingly, when two or more conductive elements 43 of opposite polarity contact a metallic prosthesis, a current flows therebetween which is sensed by current sensing circuitry 39. The output of sensing circuitry 39 is provided to display device 40, which produces an audible tone, visual display, or both that indicate the presence of the prosthesis.

Fingers 42 may be integrally formed as a band using conventional silicone tubing molding techniques, including the embedding of the thin wires within the fingers. The band may then be affixed to catheter 31 at a predetermined distance from the dilatation device using conventional techniques, such as thermowelding, gluing, etc. The ends of the thin wires nearest to the catheter 31 are coupled to leads 36 as described above. The thin wires may protrude from the distal ends of fingers 42 to form conductive elements, or alternatively, may be electrically coupled to conductive elements 43 disposed on the distal circumference of fingers 42, for example, formed of conductive films.

Alternatively, fingers 42 may be constructed to sense some other parameter, e.g., magnetic field, capacitance, etc., corresponding to a physical property of the prosthesis, as described below with respect to FIGS. 7 and 8. Further, the plurality of fingers 42 may be replaced entirely with compliant and resilient thin wires in the form of bristles, again provided that the bristles are spaced apart far enough that they do not inadvertently contact one another to generate false indications of the prosthesis location.

The present invention further includes methods of using apparatus constructed in accordance with the principles of the invention to determine the location of a previously deployed prosthesis. The following description provides illustrative methods of using the apparatus of FIG. 3 to determine the location of a previously deployed prosthesis, although the methods may be applied equally well to position a therapeutic device, for example, to position a GDC aneurysm coil or reposition or retrieve a radioactive prosthesis.

Figure 5:
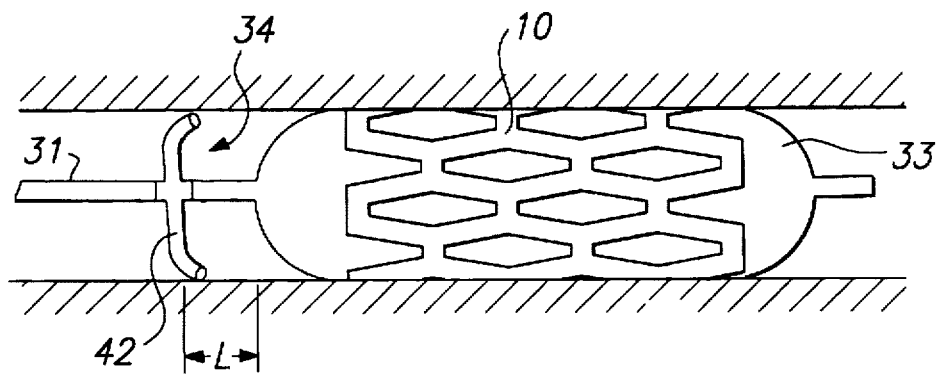
FIG. 5 is a side view of the apparatus of the present invention positioned within the prosthesis of FIG. 1.

With respect to FIG. 5, once the clinician has determined that a previously deployed prosthesis 10 must be further expanded, either because the initial expansion was incomplete or the prosthesis has become narrowed, the clinician employs apparatus 30 to accurately position dilatation device 33 within the prosthesis, thereby enabling further expansion of the prosthesis.

First, leads 36 emanating from proximal end 37 of catheter 31 are connected to apparatus 37, and power source 38 is turned on to energize conductive elements 43 disposed on fingers 42. Power source 38 preferably provides a very low voltage (about 20 Volts RMS), high frequency (about 100 MHZ) alternating current at very low amperes. As will of course be understood by those of skill in the art, the applied voltage and current should be of sufficient strength to provide a detectable signal, but of sufficiently low amperage as to not create resistive heating of the prosthesis. Suitable power sources for use in practicing the present invention are, for example, described in U.S. Pat. No. 4,492,231 and U.S. Pat. No. 5,472,443, provided that these power sources are used at very low power settings.

Catheter 31 is then inserted over guidewire 41 so that distal end region 32 of catheter 33 passes through the interior of the prosthesis. At a point during this insertion, two or more of fingers 42 of prosthesis locator sensor 34 contact the proximal edge of prosthesis 10. At the point of first contact between the two or more fingers 42 carrying conductive elements 43 of different polarity, current sensing circuit 39 detects a current flowing through the circuit. Current sensing circuitry 39, which be readily modified from that of a conventional ammeter, generates a signal proportional to the current conducted between conductive elements 43 via prosthesis 10. The signal generated by current sensing circuitry 39 is provided to display device 40, which alerts the clinician to the presence of the proximal edge of the prosthesis by emitting a tone, generating a displayed waveform, or both.

The clinician records the insertion length of catheter 31 at which the proximal edge of prosthesis 10 is first detected by prosthesis locator sensor 34. The clinician then withdraws catheter 31 proximally by a distance equal to the predetermined distance between prosthesis locator sensor 34 and dilatation device 33, thereby aligning a section of dilatation device 33 of uniform cross-section within prosthesis 10, as seen in FIG. 5. Dilatation device 33 is then expanded to uniformly expand prosthesis 10 along its length.

If necessary, the clinician may choose to deflate the dilatation device to view the re-expanded prosthesis using fluoroscopic imaging methods. If further expansion of the prosthesis is required, the clinician simply follows the steps described above to locate the proximal edge of the prosthesis and align the dilatation device for further expansion.

As will of course be apparent to one of skill in the art of catheter design, the apparatus of FIG. 3 may be modified so that prosthesis locator sensor 34 is disposed distally of the dilatation device 33, rather than proximally thereof as described with respect to FIGS. 3–5 above. If so configured, prosthesis locator sensor is disposed a predetermined distance distal of dilatation device 33. The method described hereinabove is then adapted so that catheter 31 is inserted transluminally into the body vessel until the distal edge of the prosthesis is detected.

In particular, catheter 31 is advanced so that prosthesis locator sensor 34 passes through the interior of prosthesis 10, at which the signal generated by current sensing circuitry 39 remains at a maximum value. Once prosthesis locator sensor 34 clears the distal end of prosthesis 10, the current conducted between conductive elements 43 will again drop to near zero, indicating the presence of the distal edge of the prosthesis. The clinician then reciprocates the catheter slightly to record the exact position corresponding to the distal edge of the prosthesis. The clinician then advances the catheter distally by the predetermined offset distance between the distal prosthesis locator sensor and the dilatation device, thus aligning a desired portion of the dilatation device with the prosthesis.

Figure 6:
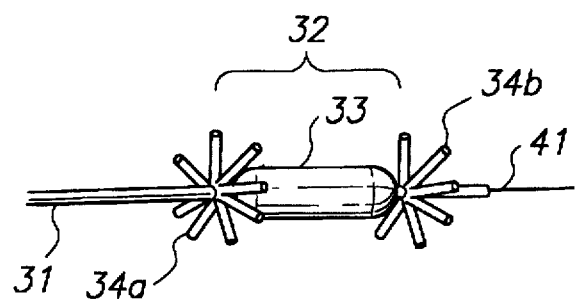
FIG. 6 is an illustrative alternative embodiment of apparatus constructed in accordance with the present invention.

Referring now to FIG. 6, an alternative embodiment of the apparatus of the present invention is described, in which components of the apparatus 30 remain unchanged except as depicted in FIG. 6. In FIG. 6, catheter 31 has distal end region 32 comprising dilatation device 33, proximal prosthesis locator sensor 34a, and distal prosthesis locator sensor 34b. Catheter 31 and prosthesis locator sensors 34a and 34b are constructed as described hereinabove, and are each electrically coupled to apparatus 37 via leads 36, so that selected ones of the each of the pluralities of fingers carry conductive elements of alternate polarity. Each of prosthesis locator sensors 34a and 34b are disposed at a predetermined offset from dilatation device 33.

The method of use of the apparatus of FIG. 6 is similar to that described above with respect to the embodiment of FIGS. 3–5. In particular, once the clinician has determined that a previously deployed prosthesis 10 must be further expanded, leads 36 emanating from proximal end 37 of catheter 31 first are connected to apparatus 37, and power source 38 is turned on to energize conductive elements 43 disposed on fingers 42 with a very low voltage, high frequency alternating current signal.

Catheter 31 is then inserted over guidewire 41 so that distal end region 32 of catheter 33 (including distal prosthesis locator sensor 34b) passes through the interior of the prosthesis. As distal prosthesis locator sensor 34b passes through the prosthesis, it will conduct a maximum current, which in turn, will cause display device 40 to output a first audible tone or visual display. At a point during continued insertion of catheter 31, two or more of fingers 42 of proximal prosthesis locator sensor 34a contact the proximal edge of prosthesis 10, this time resulting in display device 40 providing a second audible tone, vibration of the handle or visual display.

The clinician records the insertion length of catheter 31 at which distal prosthesis locator sensor 34b no longer detects the presence of the prosthesis (corresponding to the distal edge of the prosthesis), and the location of the proximal edge of the prosthesis as first detected by proximal prosthesis locator sensor 34a. Using the insertion lengths of the catheter at which these two points occur, the clinician may then move the catheter to an insertion length that is intermediate the two recorded values, thereby centering the dilatation device within the prosthesis.

In addition, the embodiment of FIG. 6 may be used advantageously where a series of prostheses are deployed in a body lumen. In this case, depending upon the result sought, the clinician may choose to align the dilatation device within the series of prostheses based upon the detected location of the distal edge of the distal-most prosthesis, based upon the proximal edge of the proximal-most prosthesis, or at any location in between.

Figure 7:
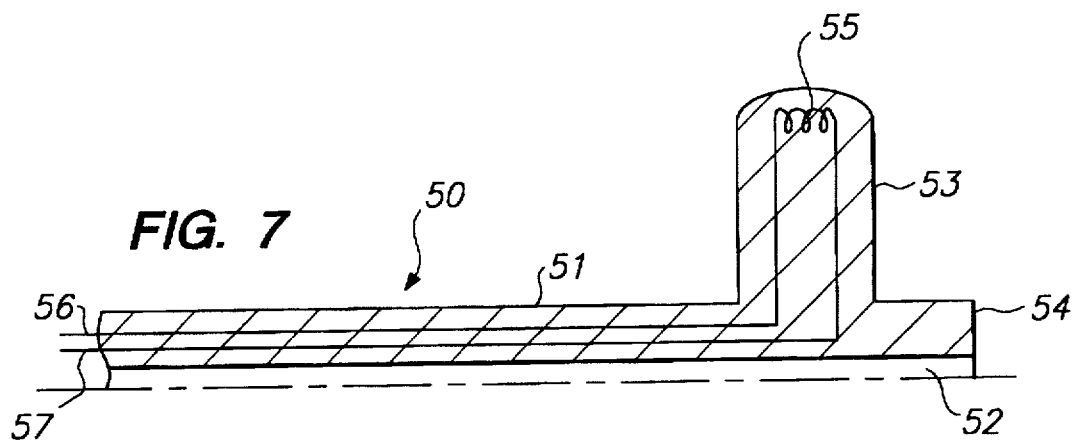
FIG. 7 is a partial sectional view of the distal end of an illustrative embodiment of apparatus constructed to sense the presence of a prosthesis using inductive techniques.
Figure 8:
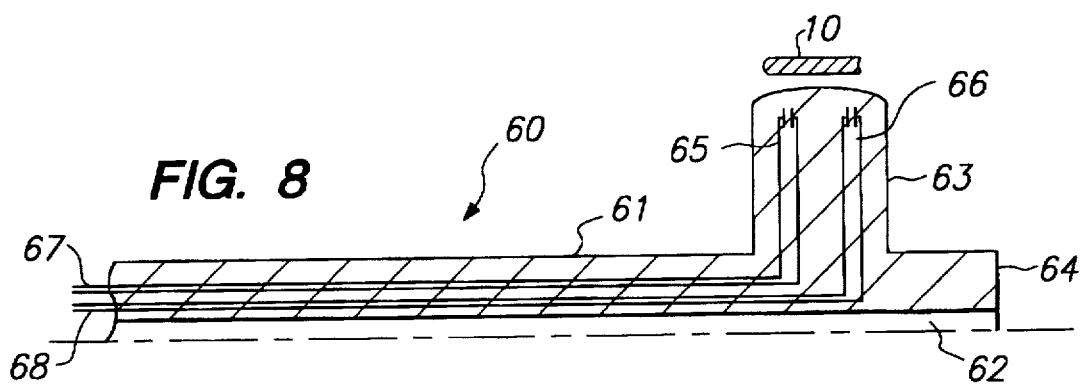
FIG. 8 is a partial sectional view of the distal end of an illustrative embodiment of apparatus constructed to sense the presence of a prosthesis using capacitive techniques.

Referring now to FIGS. 7 and 8, alternative embodiments of the apparatus of the present invention are described (wherein the dilatation portion of the device is omitted for clarity). In FIG. 7, apparatus 50 includes catheter 51 having guide wire lumen 52 and a plurality of resilient radially-projecting fingers 53 (only one shown) extending from its circumference near distal end 54. Each finger 53 includes an inductive coil 55 embedded near the tip of the finger, which is coupled via embedded wire leads 56 and 57 to suitable detector circuitry. Specifically, inductive coil 55 forms part of an oscillator circuit (not shown), so that changes in inductance caused by movement of the coil in proximity to a ferrous alloy causes a frequency change in the circuit, which is then detected. Such circuitry is conventional in the design of metal detector circuits used for treasure hunting, as described, for example, in Encyclopedia of Electronic Circuits, Vols. 1–6 (edited by Rudolf Graf and William Sheets), McGraw-Hill (1996) and its extension to the present invention will be apparent to one of skill in the art of analog circuit design.

The apparatus of FIG. 7 may be advantageously used to determine a previously deployed prosthesis, such as an aneurysm treatment coil, without direct electrical contact being established between the prosthesis locator sensor and the prosthesis. Thus, for example, apparatus 50 may be employed by a clinician to accurately determine the location of a previously deployed aneurysm treatment coil, after which the clinician could insert further aneurysm treatment coils into the aneurysm. Accordingly, apparatus 50 may include a therapeutic device, e.g., for deploying an aneurysm treatment coil, either disposed from the distal end of the catheter (similar to FIG. 3), or may include a two-part arrangement as described hereinbelow with respect to FIG. 9.

With respect to FIG. 8, apparatus 60 includes catheter 61 having guide wire lumen 62 and a plurality of resilient radially-projecting fingers 63 (only one shown) extending from its circumference near distal end 64. Each finger 63 includes a pair of capacitors 65 and 66 embedded near the tip of the finger, which are coupled via embedded wire leads 67 and 68 to suitable detector circuitry. Capacitors 65 and 66 also form part of an oscillator circuit, so that changes in capacitance caused by movement of the finger 63 in proximity to a ferrous alloy (portion of prosthesis 10) causes a frequency change, which is then detected. Such circuitry for detecting capacitance changes is per se known in the art, and is similar in design to that described above with respect to FIG. 7. Apparatus 60 may be advantageously used with other therapeutic devices, apart from dilatation devices, to effectuate treatment involving positioning of the therapeutic device with respect to a previously deployed prosthesis.

Figure 9:
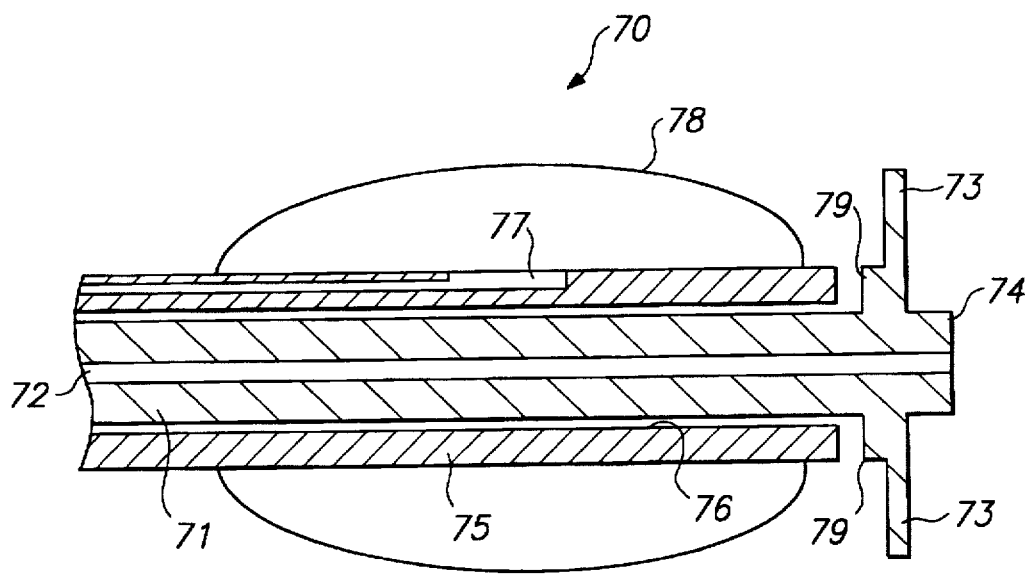
FIG. 9 is a sectional view of the distal end of apparatus constructed in accordance with the present invention in which a dilatation device is disposed on a catheter separate from that carrying the prosthesis locator sensors.

Referring now to FIG. 9, an alternative embodiment of the apparatus of the present invention is described. Apparatus 70 includes catheter 71 having guidewire lumen 72 and plurality of radially outwardly projecting resilient fingers 73 disposed near distal end 74. Fingers 73 include prosthesis locator sensors that detect the presence of a previously deployed prosthesis by direct electrical connection, inductance, capacitance, or by the detection of some other physical property of the prosthesis, as described hereinabove. Apparatus 70 further includes dilatation catheter 75 having lumen 76 suitable for sliding movement of catheter 75 over catheter 71. Catheter 71 includes balloon member 78 which is inflated via inflation lumen 77. Fingers 73 of catheter 71 may include base portions 79 having increased thickness that serve as a stop for distal travel of catheter 75 over catheter 71.

The apparatus of FIG. 9 is used in a fashion similar to that of the other embodiments described hereinabove. In particular, catheter 71 is first advanced along a guidewire (not shown) so that the prosthesis locator sensors mounted on fingers 73 detect the presence of a previously deployed prosthesis. Catheter 71 is then advanced through the prosthesis to locate the distal most edge of the prosthesis. Catheter 71 is held in position while catheter 75 is advanced along catheter 71. Balloon member 78 may then be expanded to further expand the prosthesis, as described hereinabove.

While preferred illustrative embodiments of the invention are described above, it will be obvious to one skilled in the art that various changes and modifications may be made therein without departing from the invention and the appended claims are intended to cover all such changes and modifications which fall within the true spirit and scope of the invention.

What is claimed is:

1. Apparatus for detecting the location of a prosthesis previously deployed in a body lumen and for treating same, the apparatus for use in combination with an indicator means for providing a sensory indication, the apparatus comprising:

a catheter having a distal end region;

a therapeutic device disposed on the distal end region for effecting treatment in association with the prosthesis;

a first sensor disposed on the distal end region adjacent to the therapeutic device to detect an edge of the prosthesis; and means for coupling the first sensor to the indicator means.

2. The apparatus as defined in claim 1 wherein the first sensor is disposed on the distal end region at a location proximal of the therapeutic device.

3. The apparatus as defined in claim 2 wherein the first sensor is spaced apart from the therapeutic device a predetermined distance.

4. The apparatus as defined in claim 1 wherein the first sensor is disposed on the distal end region at a location distal of the therapeutic device.

5. The apparatus as defined in claim 4 wherein the first sensor is spaced apart from the therapeutic device a first predetermined distance.

6. The apparatus as defined in claim 1 further comprising a second sensor disposed on the distal end region, the second sensor disposed at a location distal of the therapeutic device.

7. The apparatus as defined in claim 1 further comprising a power source, wherein the first sensor comprises at least two compliant and resilient fingers projecting from the circumference of the catheter, the at least two compliant and resilient fingers carrying conductive elements electrically coupled to the power supply.

8. The apparatus as defined in claim 1 further comprising detector circuitry, wherein the first sensor comprises a compliant and resilient finger projecting from the circumference of the catheter, and the compliant and resilient finger carries a coil coupled to the detector circuitry to detect a change in inductance when in proximity to a ferrous alloy.

9. The apparatus as defined in claim 1 further comprising detector circuitry, wherein the first sensor comprises a compliant and resilient finger projecting from the circumference of the catheter, and the compliant and resilient finger carries a capacitor coupled to the detector circuitry to detect a change in capacitance when in proximity to a ferrous alloy.

10. The apparatus as defined in claim 1 wherein the therapeutic device comprises an inflatable balloon.

11. Apparatus for detecting the location of a prosthesis previously deployed in a body lumen, the apparatus adapted for use in conjunction with a catheter-based therapeutic device, the apparatus comprising:

a first catheter having a distal end region, the catheter having an exterior diameter suitable for accepting the catheter-based therapeutic device thereover;

a first sensor disposed on the distal end region for detecting an edge of the prosthesis;

indicator circuitry for providing an indication of the presence of an edge of a prosthesis; and means for coupling the first sensor to the indicator circuitry.

12. The apparatus as defined in claim 11 wherein the first sensor comprises a plurality of compliant and resilient fingers projecting from the circumference of the catheter.

13. The apparatus as defined in claim 12 further comprising a power source and first and second conductive elements disposed from at least some of the plurality of compliant and resilient fingers, the first and second conductive elements coupled to the power source.

14. The apparatus as defined in claim 11 in combination with a catheter-based therapeutic device adapted to be slidably disposed on the first catheter to selectively expand the diameter of the prosthesis.

15. A method of positioning a therapeutic device in relation to a prosthesis previously deployed in a body lumen, the method comprising steps of:

providing a catheter having a distal end region, a sensor disposed in the end region, and a therapeutic device disposed at a predetermined distance from the sensor;

inserting the catheter transluminally until the sensor detects a desired edge of the prosthesis; and moving the catheter through a distance substantially equal to the predetermined distance to obtain a desired offset between the sensor and the prosthesis.

16. The method as defined in claim 15 wherein the step of providing a catheter comprises a step of providing a catheter having a sensor disposed between first and second conductive elements, the method further comprising steps of:

coupling the first and second conductive elements to a power source that energizes the first and second conductive elements; and conducting a current through the sensor between the first and second conductive elements.

17. The method as defined in claim 16 wherein the step of conducting a current through the sensor consists of a step of conducting a current through the prosthesis by direct electrical contact or conducting a sense current through a coil or capacitor to detect inductance or capacitance changes.

18. The method as defined in claim 15 further comprising a step of recording a length of the catheter insertion at which the sensor detects a desired edge of the prosthesis.

19. The method as defined in claim 15 wherein the therapeutic device is a dilatation device, the method further comprising a step of expanding the dilatation device to further expand the prosthesis.

20. The method as defined in claim 15 wherein the step of providing a catheter comprises a step of providing a catheter having the sensor located proximally of the therapeutic device and the step of moving the catheter through a distance comprises a step of moving the catheter proximally through a distance substantially equal to the predetermined distance.

21. The method as defined in claim 15 wherein the step of providing a catheter comprises a step of providing a catheter having the sensor located distally of the therapeutic device and the step of moving the catheter through a distance comprises a step of moving the catheter distally through a distance substantially equal to the predetermined distance.

* * * * *